(12) United States Patent
Morito et al.

(10) Patent No.: US 9,061,086 B2
(45) Date of Patent: Jun. 23, 2015

(54) PHOTOCATALYST ELEMENT STRUCTURE, ULTRAVIOLET RADIATION AIR PURIFICATION SYSTEM, PHOTOCATALYST SHEET, AND METHOD OF MANUFACTURING PHOTOCATALYST SHEET

(75) Inventors: Yuko Morito, Meguro-ku (JP); Akira Fujishima, Kawasaki (JP); Takuji Horie, Niigata (JP); Kazuya Nakata, Kawasaki (JP); Taketoshi Murakami, Kawasaki (JP); Tsuyoshi Ochiai, Kawasaki (JP)

(73) Assignees: U-VIX Corporation, Tokyo (JP); Kanagawa Academy of Science and Technology, Kanagawa (JP)

(*) Notice: Subject to any disclaimer, the term of this patent is extended or adjusted under 35 U.S.C. 154(b) by 641 days.

(21) Appl. No.: 13/394,755

(22) PCT Filed: Aug. 5, 2010

(86) PCT No.: PCT/IB2010/002221
§ 371 (c)(1),
(2), (4) Date: Mar. 7, 2012

(87) PCT Pub. No.: WO2011/092541
PCT Pub. Date: Aug. 4, 2011

(65) Prior Publication Data
US 2012/0171079 A1   Jul. 5, 2012

(30) Foreign Application Priority Data

Jan. 26, 2010 (JP) ................................ 2010-014624
Mar. 4, 2010 (JP) ................................ 2010-047773

(51) Int. Cl.
*A61L 9/20* (2006.01)
*A61L 2/08* (2006.01)
*B01J 21/06* (2006.01)
*B01J 35/00* (2006.01)
*B01J 35/04* (2006.01)

(52) U.S. Cl.
CPC ................ *A61L 9/205* (2013.01); *A61L 2/088* (2013.01); *A61L 9/20* (2013.01); *A61L 2209/10* (2013.01); *B01J 21/063* (2013.01); *B01J 35/004* (2013.01); *B01J 35/04* (2013.01)

(58) Field of Classification Search
CPC .................................. A61L 9/20; B01J 37/02
USPC ......................................................... 422/121
See application file for complete search history.

(56) References Cited

U.S. PATENT DOCUMENTS

| | | |
|---|---|---|
| 5,364,586 A | 11/1994 | Trusov et al. |
| 6,238,631 B1 | 5/2001 | Ogata et al. |
| 6,531,100 B1 | 3/2003 | Ogata et al. |
| 2008/0090719 A1 | 4/2008 | Wada et al. |

FOREIGN PATENT DOCUMENTS

| | | |
|---|---|---|
| EP | 0 911 078 A1 | 4/1999 |
| EP | 0 993 859 A1 | 4/2000 |
| EP | 1 813 688 A1 | 8/2007 |
| JP | 2001-205099 A | 7/2001 |

OTHER PUBLICATIONS

International Search Report issued in PCT/IB2010-002221 dated Feb. 7, 2011 (5 pages).

*Primary Examiner* — Sean E Conley
(74) *Attorney, Agent, or Firm* — Procopio, Cory, Hargreaves & Savitch LLP

(57) ABSTRACT

A photocatalyst element structure includes a photocatalyst element that includes a flat photocatalyst sheet and an undulating photocatalyst sheet overlapped on the flat photocatalyst sheet. The flat photocatalyst sheet and the undulating photocatalyst sheet include a porous titanium foil having a non-periodic spongy structure impregnated with anatase titanium dioxide particles. The photocatalyst element structure can include a plurality of the photocatalyst elements so that the flat photocatalyst sheet and the undulating photocatalyst sheet alternate.

14 Claims, 10 Drawing Sheets

US 9,061,086 B2

PHOTOCATALYST ELEMENT STRUCTURE, ULTRAVIOLET RADIATION AIR PURIFICATION SYSTEM, PHOTOCATALYST SHEET, AND METHOD OF MANUFACTURING PHOTOCATALYST SHEET

TECHNICAL FIELD

The present invention relates to a photocatalyst element structure impregnated with anatase titanium dioxide particles as a photocatalyst and an ultraviolet radiation air purification system that employs the photocatalyst element structure. The present invention also relates to a photocatalyst sheet and a method of manufacturing the photocatalyst sheet.

BACKGROUND ART

Titanium dioxide in anatase form is known to function as a photocatalyst. When titanium dioxide is exposed to ultraviolet radiation, it produces active species, such as hydroxy radicals, and holes, and breaks apart an organic material. Breaking apart of the organic material produces deodorization and sterilizing effects, and therefore, titanium dioxide is often used in air purification systems.

FIG. 15 illustrates a conventional fluid purification system 31 that has been disclosed, for example, in Japanese Patent Application Laid-open No. H11-276558. The conventional fluid purification system 31 includes a casing 32, and a light source 33 and a photocatalyst structure 34 are arranged inside the casing 32.

The photocatalyst structure 34 surrounds the light source 33. The photocatalyst structure 34 includes a plurality of cylindrical photocatalyst bodies 35 having different diameters. The cylindrical photocatalyst bodies 35 are arranged coaxially at equal intervals and a not shown spacer is arranged between the adjacent cylindrical photocatalyst bodies 35. The cylindrical photocatalyst body 35 is made of a metallic mesh impregnated with a photocatalyst. In this conventional art, the photocatalyst structure 34 is a three-fold structure having three coaxially arranged cylindrical photocatalyst bodies 35.

CITATION LIST

Patent Literature

Japanese Patent Application Laid-open No. H11-276558

SUMMARY OF THE INVENTION

Technical Problem

However, it was found that the hazardous odoriferous substances cannot be effectively decomposed with the conventional photocatalyst structure. One cause of this could be as follows. When a plurality of the conventional cylindrical photocatalyst bodies is arranged in an overlapping manner, the periodically repeating geometrical patterns of the adjacent cylindrical photocatalyst bodies interfere and create a moire pattern having fine and coarse portions. The intensity of ultraviolet radiation drops at the locations of the coarse portions leading to a reduction in the purification performance.

As shown in (a) in FIG. 16, the conventional cylindrical photocatalyst body 35 has holes in between crisscrossing wires 36 that form the mesh structure and has a high porosity. When air passes through the cylindrical photocatalyst body 35 at substantially the centers of these holes, the air does not come in contact with the photocatalyst at all. Therefore, the desired purification effect cannot be obtained.

Moreover, the air passes six times through the cylindrical photocatalyst bodies 35 when it passes through the innermost cylindrical photocatalyst body 35. However, it is believed that the amount of air that passes through the cylindrical photocatalyst bodies at substantially the centers of the holes without coming in contact with the photocatalyst is considerably high.

Moreover, because a plurality of the cylindrical photocatalyst bodies 35 is arranged coaxially with spacers in between, two-dimensional arc-shaped spaces are formed between the adjacent cylindrical photocatalyst bodies 35. As shown in (b) in FIG. 16, when air passes through these arc-shaped spaces, the chances are higher that the air does not come in contact with the photocatalyst at all, so that the desired purification effect cannot be obtained.

When a coating of anatase titanium dioxide is directly applied onto an ordinary metallic mesh or a metallic net, because the bonding strength of titanium dioxide with a metallic surface is weak, the coating of anatase titanium dioxide peels off easily from the metallic surface.

In order to increase the surface area, the cylindrical photocatalyst bodies 35 are generally made of metallic meshes in which thin wires are woven finely. Such metallic meshes have very weak mechanical strength and therefore, the cylindrical photocatalyst bodies 35 collapse when they are even just grasped with a hand. Thus, the conventional photocatalyst bodies 35 were difficult to handle and assemble.

Moreover, if the cylindrical photocatalyst body 35 is held in a hand by grasping its outer circumferential surface, the titanium dioxide coating peels off easily in a wide area.

In addition, a spacer is required in between the adjacent cylindrical photocatalyst bodies 35. In other words, number of parts increases leading to an increase in the manufacturing costs.

Thus, there is a need and room for improvement in the conventional technology.

Solution to Problem

A photocatalyst element structure according to an aspect of the present invention includes a photocatalyst element that includes a flat photocatalyst sheet and an undulating photocatalyst sheet overlapped on the flat photocatalyst sheet. The flat photocatalyst sheet and the undulating photocatalyst sheet include a porous titanium foil having a non-periodic spongy structure impregnated with anatase titanium dioxide particles.

An ultraviolet radiation air purification system according to another aspect of the present invention includes a casing having an air inlet and an air outlet; a photocatalyst element structure that is arranged inside the casing and that is impregnated with anatase titanium dioxide particles as a photocatalyst for purifying air inside the casing; and an ultraviolet radiation source that irradiates ultraviolet radiation on the photocatalyst element structure to activate the photocatalyst. The photocatalyst element structure includes a photocatalyst element including a flat photocatalyst sheet and an undulating photocatalyst sheet overlapped on the flat photocatalyst sheet, and the flat photocatalyst sheet and the undulating photocatalyst sheet include a porous titanium foil having a non-periodic spongy structure impregnated with the anatase titanium dioxide particles.

A photocatalyst sheet according to still another aspect of the present invention includes a porous titanium foil having a non-periodic spongy structure in which a number of minute cavities that communicate from one surface to other surface of the porous titanium foil; a titanium oxide base formed on the porous titanium foil with an anodized film; and a photocatalyst film formed by baking anatase titanium dioxide particles on the titanium oxide base.

A method of manufacturing a photocatalyst sheet according to still another aspect of the present invention includes a first step of forming a porous titanium foil having a non-periodic spongy structure in which a number of minute cavities communicate from one surface to other surface of the porous titanium foil; a second step of forming a titanium oxide base on the porous titanium foil; and a third step of forming a photocatalyst layer on the titanium oxide base.

DESCRIPTION OF EMBODIMENTS

Exemplary embodiments of the present invention are described in detail below with reference to the accompanying drawings. It should be noted that the present invention is by no way limited to the embodiments described below.

Figure 1:
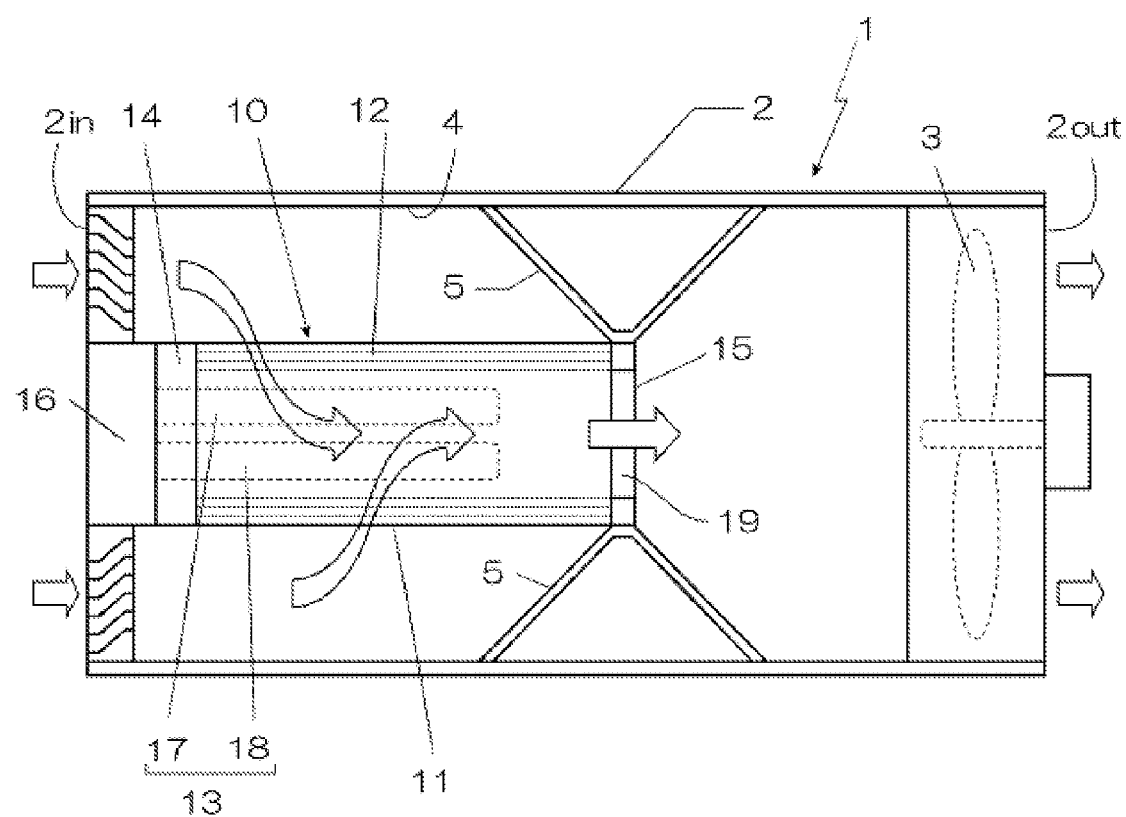
FIG. 1 illustrates an ultraviolet radiation air purification system according to a first embodiment of the present invention.

FIG. 1 illustrates an ultraviolet radiation air purification system 1 according to a first embodiment of the present invention. The ultraviolet radiation air purification system 1 includes a casing 2, and a photocatalyst unit 10 is arranged inside the casing 2. The casing 2 is provided with an air inlet 2 in on one side to take air inside the casing 2 and an air outlet 2 out on the other side to discharge the air outside of the casing 2.

An exhaust fan 3 is arranged near the air outlet 2 out. When the exhaust fan 3 is turned on, air currents that flow from the air inlet 2 in toward the air outlet 2 out are generated inside the casing 2. The position of the exhaust fan 3 is not limited to the one shown in FIG. 1. The exhaust fan 3 can be arranged at such a position where it can effectively generate air currents inside the casing 2.

The photocatalyst unit 10 is arranged in the path of the air that flows from the air inlet 2 in toward the air outlet 2 out, and it includes a centrally hollow cylindrical photocatalyst structure 12 and an ultraviolet radiation source 13 arranged inside the hollow of the photocatalyst structure 12. The photocatalyst structure 12 includes a photocatalyst element structure 11.

Figure 2:
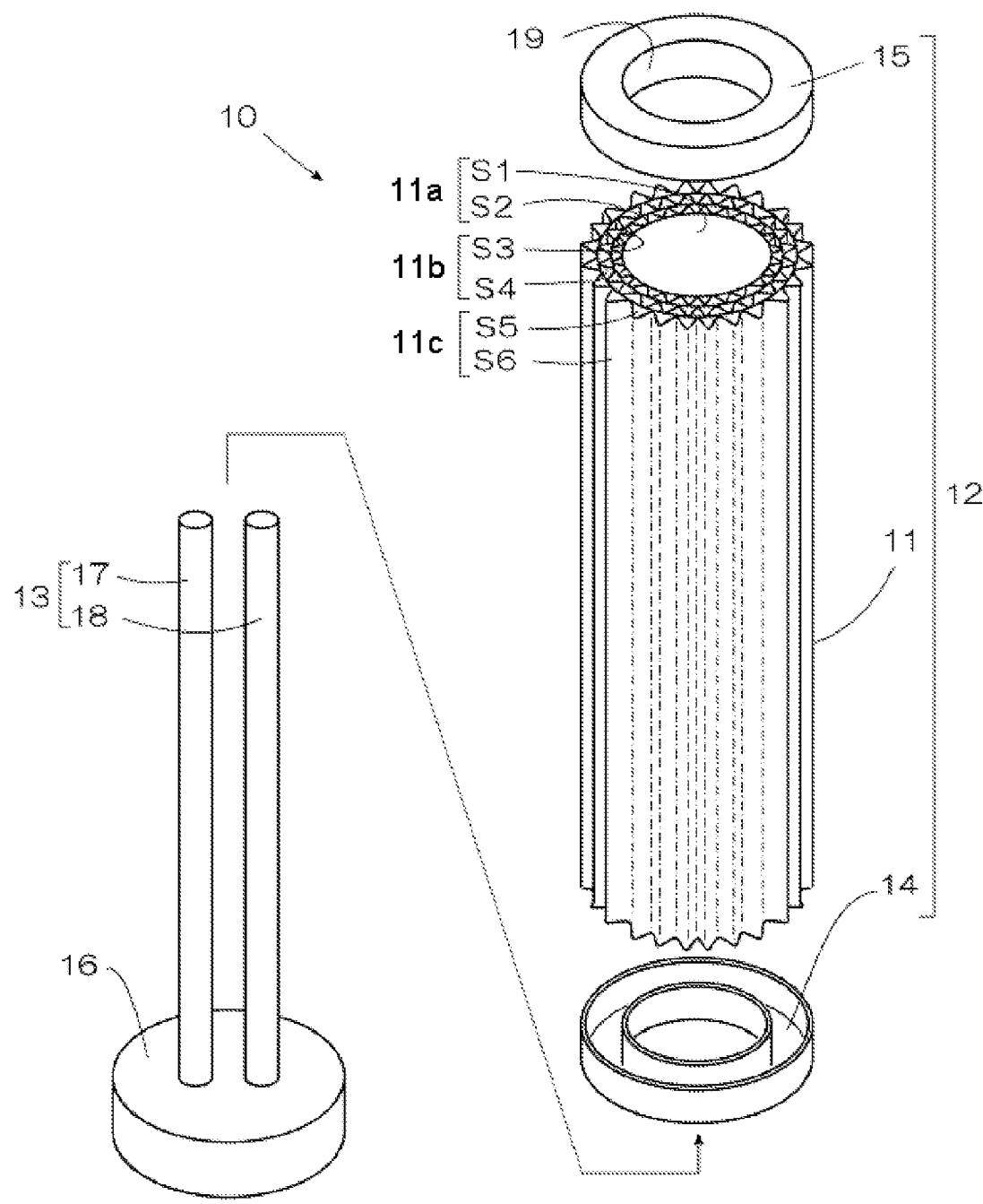
FIG. 2 is an exploded view of a photocatalyst unit shown in FIG. 1.

As shown in FIG. 2, the photocatalyst element structure 11 includes three overlapping photocatalyst elements 11a, 11b, and 11c rolled in a centrally hollow cylindrical shape. Each of the photocatalyst elements includes a flat photocatalyst sheet and an undulating photocatalyst sheet arranged on the flat photocatalyst sheet. The thickness of the flat photocatalyst sheet and the undulating photocatalyst sheet is between about 200 micrometers (μm) to about 300 μm. The undulating photocatalyst sheet has substantially parallel alternating ridges and trenches that run continuously, for example, in the direction of a central axis of the cylindrical photocatalyst element structure 11.

More specifically, the innermost photocatalyst element 11a includes a flat photocatalyst sheet S1 and an undulating photocatalyst sheet S2 arranged on the flat photocatalyst sheet S1, the intermediate photocatalyst element 11b includes a flat photocatalyst sheet S3 and an undulating photocatalyst sheet S4 arranged on the flat photocatalyst sheet S3, and the outermost photocatalyst element 11c includes a flat photocatalyst sheet S5 and an undulating photocatalyst sheet S6 arranged on the flat photocatalyst sheet S5.

Each of the photocatalyst sheets S1 to S6 is made of a porous titanium foil having a non-periodic spongy structure impregnated with anatase titanium dioxide particles. The porous titanium foil is prepared by performing etching processing in non-periodic patterns from both the surfaces of a titanium foil; however, it can be prepared by performing etching processing in non-periodic patterns from one surface of a titanium foil.

Figure 5:
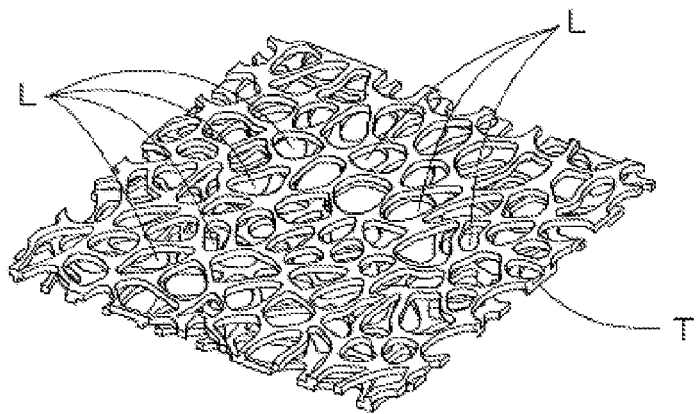
FIG. 5 is an enlarged schematic perspective view of a porous titanium foil.

Particularly, no periodicity is produced when the non-periodic spongy structure is formed by performing etching processing from both the surfaces of the titanium foil. In other words, when the etching processing is performed from both the surfaces of the titanium foil, as shown in FIG. 5, minute cavities of various shapes and sizes are formed on the surfaces of the titanium foil to produce a porous titanium foil T. As a result, complicated labyrinth channels L are produced in the thickness direction of the porous titanium foil T and the surface area increases as compared to a simple mesh structure. The porosity of each of the photocatalyst sheets S1 to S6 is between about 50% to about 80%.

Subsequently, each of the photocatalyst sheets S1 to S6 is dipped into a slurry containing the anatase titanium dioxide particles whereby the anatase titanium dioxide particles adhere to the surfaces of the photocatalyst sheets S1 to S6. Each of the photocatalyst sheets S1 to S6 is then baked and dried. As a result, a coating of anatase titanium dioxide is formed on both the surfaces of the porous titanium foil T as well as on internal walls of the labyrinth channels L of the porous titanium foil T of each of the photocatalyst sheets S1 to S6.

Figure 3:
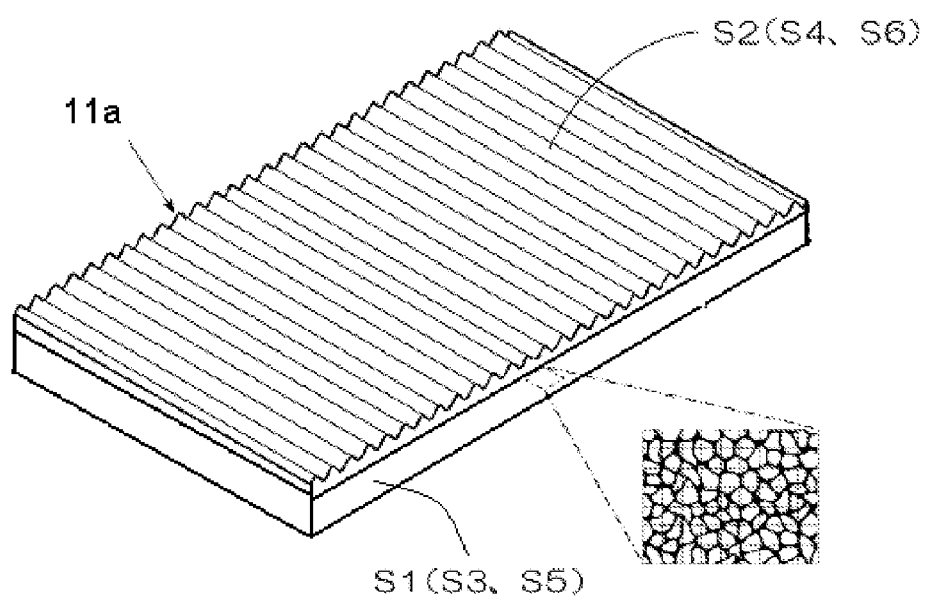
FIG. 3 is an enlarged perspective view of a photocatalyst element shown in FIG. 2.

Subsequently, as shown in FIG. 3, in the photocatalyst element 11a, the undulating photocatalyst sheet S2 having a rectangular shape and impregnated with the anatase titanium dioxide particles is overlapped on the flat photocatalyst sheet S1 having a rectangular shape and impregnated with the anatase titanium dioxide particles. The undulating photocatalyst sheet S2 is made by press processing a not shown flat photocatalyst sheet that is longer than the flat photocatalyst sheet S1. In this manner, the photocatalyst element 11a that is planar in shape is obtained. The photocatalyst elements 11b and 11c that are planar in shape are obtained in a similar manner.

Figure 4:
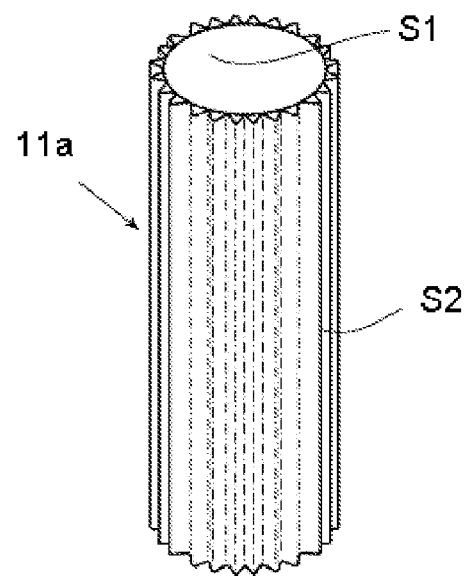
FIG. 4 is a perspective view of the photocatalyst element shown in FIG. 3 when it is rolled in a cylindrical shape.

Then, as shown in FIG. 4, the planar photocatalyst element 11a is rolled to obtain the photocatalyst element 11a having a centrally hollow cylindrical shape. Subsequently, the photocatalyst element 11b is rolled around the photocatalyst element 11a and the photocatalyst element 11c is rolled around the photocatalyst element 11b to obtain the centrally hollow cylindrical photocatalyst element structure 11. In the cylindrical photocatalyst element structure 11, the undulating photocatalyst sheet S6 of the photocatalyst element 11c is located at its outer periphery, the flat photocatalyst sheet S1 of the photocatalyst element 11a is located at its inner periphery, and they are exposed to the outside.

The photocatalyst element 11b is made in a dimension such that, when it is rolled around the photocatalyst element 11a, no gap is generated at the joint of the edges of the photocatalyst element 11b. The photocatalyst element 11c is also made in a similar manner.

It should be noted that the number of the photocatalyst elements in the photocatalyst element structure 11 is not limited to three. The photocatalyst element structure 11 can have less than three or more than three photocatalyst elements. The photocatalyst elements can be overlapped to the extent that ultraviolet radiation leaks from the inside to the outside of the photocatalyst element structure 11.

Then, as shown in FIG. 2, a ring member 14 is fit into one end and a ring member 15 is fit into the other end of the photocatalyst element structure 11, thereby obtaining the photocatalyst structure 12.

The ultraviolet radiation source 13 includes a sterilization lamp 17 and an ozone generation lamp 18. The central wavelength of the sterilization lamp 17 is 254±10 nanometers (nm) and the central wavelength of the ozone generation lamp 18 is 185±10 nm. One end of each of the sterilization lamp 17 and the ozone generation lamp 18 is fit to a base plate 16 and the other end is inserted in the hollow portion of the cylindrical photocatalyst structure 12. In this manner, the end of the photocatalyst unit 10 to which the ring member 14 has been fit is closed by the base plate 16 so that air does not enter through that end, and the other end to which the ring member 15 has been fit has a vent 19.

Then, as shown in FIG. 1, the photocatalyst unit 10 is fit inside the casing 2 with the central axis thereof substantially aligned to the general direction of the air currents flowing inside the casing 2 and the base plate 16 being arranged toward the air inlet 2in. A venture-shaped guide member 5 is provided on the internal wall of the casing 2.

The operation of the ultraviolet radiation air purification system 1 is explained below.

When the ultraviolet radiation source 13 and the exhaust fan 3 are turned on, air currents that flow from the air inlet 2in toward the air outlet 2out are generated inside the casing 2. The guide member 5 guides the air toward the photocatalyst structure 12 so that the air passes through the photocatalyst structure 12. The air comes out of the vent 19 and it is finally discharged from the air outlet 2 out to the outside of the ultraviolet radiation air purification system 1. The photocatalyst that has been impregnated in each of the photocatalyst sheets S1 to S6 is activated by the ultraviolet radiation generated by the ultraviolet radiation source 13. When the air passes through the photocatalyst sheets S6 to S1, it comes into contact with the photocatalyst, and the air is purified by a photocatalytic action.

The ozone generation lamp 18 produces ozone, and the casing 2 is filled with this ozone. Air inside the casing 2 is also purified by the action of the ozone. In other words, the air is purified even if it does not come in contact with the photocatalyst.

The photocatalyst element structure 11 has a structure in which the flat photocatalyst sheets S1, S3, and S5, and the undulating photocatalyst sheets S2, S4, and S6 are alternately overlapped. Moreover, when seen in a cross section, the photocatalyst element structure 11 has a honeycomb structure having numerous minute cells. In addition, the photocatalyst sheets S1 to S6 have a non-periodic spongy structure. As a result, when seen microscopically, the photocatalyst sheets S1 to S6 have portions through which air can pass easily and portions through which air cannot pass easily.

Figure 6:
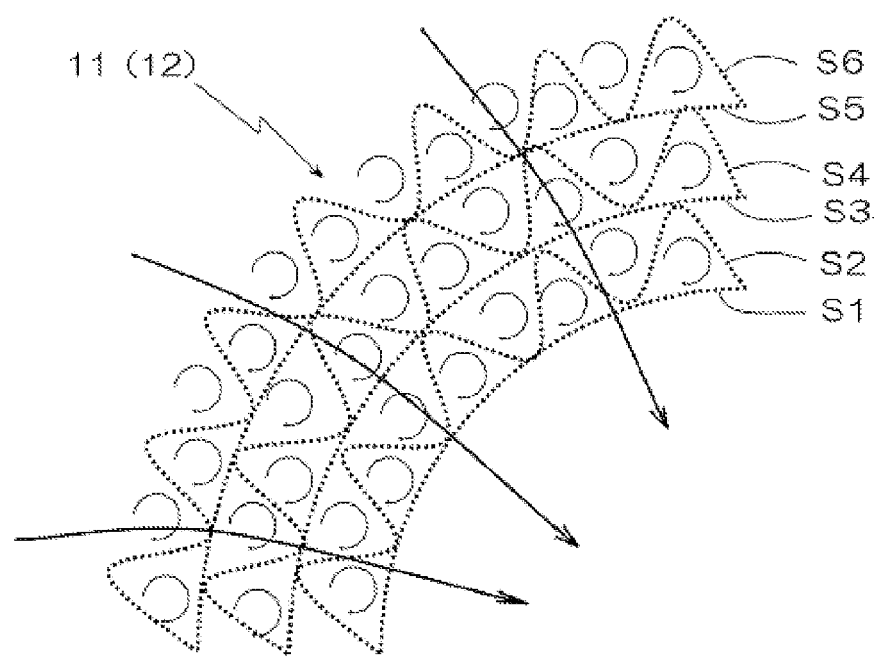
FIG. 6 is a partial top view depicting how air passes through a photocatalyst element structure.

Therefore, as shown in FIG. 6, when air passing from the outer periphery to the inner periphery of the cylindrical photocatalyst element structure 11 (the photocatalyst structure 12) enters into the minute cells of the honeycomb structure, air disturbance is produced; because, the air tries to flow toward the portions through which it can pass easily from the portions through which it cannot pass easily. In some cases, air turbulence is also produced inside the minute cells. The chances of the air coming in contact with the photocatalyst impregnated in the photocatalyst sheets S1 to S6 increase because of such air disturbance and air turbulence, and the chances that the air does not come in contact with the photocatalyst when passing through the photocatalyst sheets S1 to S6 are slim to nil. That is, the air is surely purified when it passes through the photocatalyst sheets S1 to S6.

Because the photocatalyst sheets S1 to S6 have the honeycomb structure, they do not collapse easily when they are grasped with a hand so that peeling of the coating of anatase titanium dioxide due to shape deformation does not occur easily.

Moreover, the bonding strength of a titanium foil with titanium dioxide functioning as a photocatalyst is high. Therefore, when a coating of anatase titanium dioxide is formed on the porous titanium foil, the coating does not peel off easily.

Figure 7:
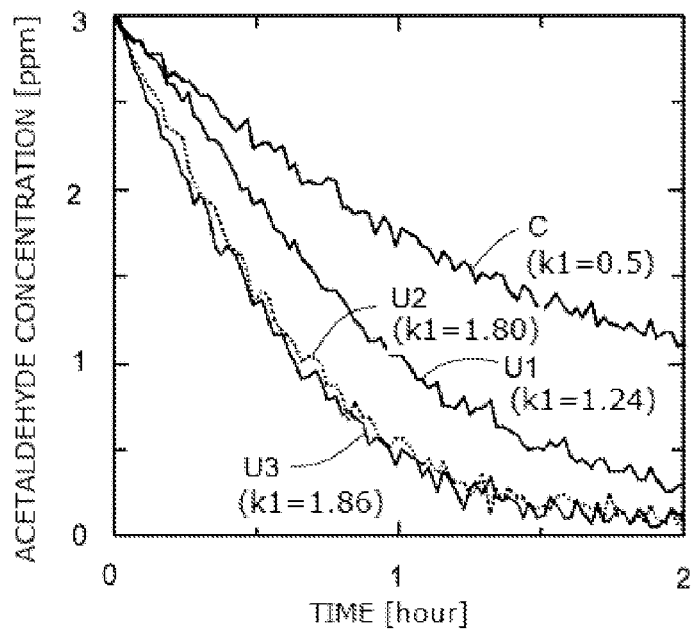
FIG. 7 is a graph for explaining experimental results.

FIG. 7 is a graph for explaining the results obtained in an experiment for verifying the performance of the photocatalyst unit 10. In this experiment, the photocatalyst unit 10 was placed inside a 1-cubic-meter enclosed space, air was blown on the photocatalyst unit 10 at a speed of 1.5 m/s, and a change in the concentration of acetaldehyde over time in the enclosed space was monitored. From the result obtained in the monitoring, a decomposition factor k1 was calculated for the photocatalyst unit 10.

This experiment was conducted on three specimen photocatalyst units. The first specimen was made with a photocatalyst element structure that included only the photocatalyst element 11a. The second specimen was made with a photocatalyst element structure that included only the photocatalyst elements 11a and 11b. The third specimen was made with a photocatalyst element structure that included all the photocatalyst elements 11a, 11b, and 11c. In FIG. 7, curves U1, U2, and U3 represent the experimental result for the first specimen, the second specimen, and the third specimen, respectively.

Moreover, the same experiment was conducted on a fourth specimen including a photocatalyst element made by applying anatase titanium dioxide on the surface of a cylindrical perforated metal sheet. A curve C in FIG. 7 represents the experimental result for the fourth specimen.

The ultraviolet radiation transmittance of the first specimen, the second specimen, the third specimen, and the fourth specimen was 4%, 0.5%, 0.05%, and 28%, respectively.

The decomposition factor k1 for the first specimen, the second specimen, the third specimen, and the fourth specimen was 1.24, 1.80, 1.86, and 0.5, respectively. That is, the decomposition factors for the first specimen, the second specimen, and the third specimen were considerably higher than that for the fourth specimen. Particularly, the decomposition factor k1 for the second specimen and the third specimen was 1.80 and 1.86, respectively, which points that these specimens exhibited excellent purification performance.

Moreover, the same experiment was conducted on a fifth specimen including a photocatalyst element structure having four photocatalyst elements, i.e., four flat photocatalyst sheets and four undulating photocatalyst sheets. The ultraviolet radiation transmittance of the fifth specimen was 0.01%. Although a curve for the fifth specimen is not shown in FIG. 7, the decomposition factor k1 for the fifth specimen was 1.28.

Thus, the third specimen exhibited the best purification performance among all the specimens.

Figure 8:
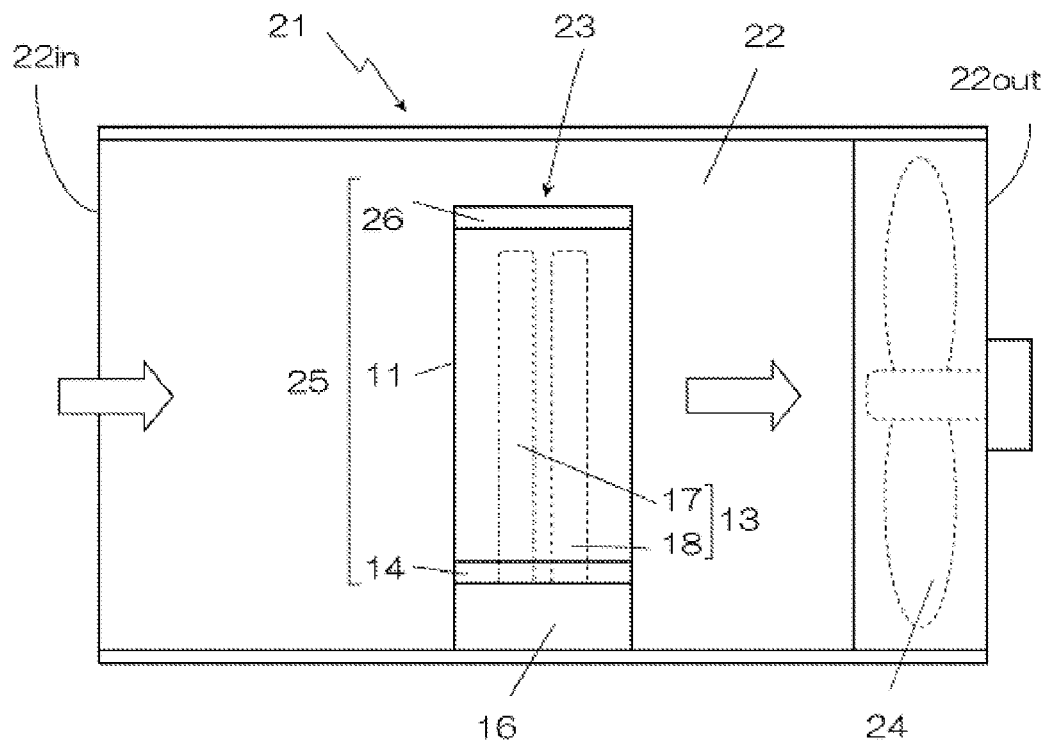
FIG. 8 illustrates an ultraviolet radiation air purification system according to a second embodiment of the present invention.

FIG. 8 illustrates an ultraviolet radiation air purification system 21 according to a second embodiment of the present invention. The ultraviolet radiation air purification system 21 includes a casing 22 and a photocatalyst unit 23 arranged inside the casing 22. The casing 22 is provided with an air inlet 22in on one side to take air inside the casing 22 and an air outlet 22out on the other side to discharge the air outside of the casing 22.

An exhaust fan 24 is arranged near the air outlet 22out. When the exhaust fan 24 is turned on, air currents that flow from the air inlet 22in toward the air outlet 22out are generated inside the casing 22.

The photocatalyst unit 23 is arranged in the path of the air that flows from the air inlet 22in toward the air outlet 22out. The photocatalyst unit 23 includes a centrally hollow cylindrical photocatalyst structure 25 and the ultraviolet radiation source 13 arranged inside the hollow of the photocatalyst structure 25. The photocatalyst structure 25 includes the photocatalyst element structure 11 according to the first embodiment.

The ultraviolet radiation source 13 includes the sterilization lamp 17 and the ozone generation lamp 18. One end of each of the sterilization lamp 17 and the ozone generation lamp 18 is fit to a base plate 16 and the other end is inserted in the hollow portion of the cylindrical photocatalyst structure 25. A disc-shaped member 26 is fit to the other end of the photocatalyst structure 25.

In other words, the structure according to the second embodiment differs from the structure according to the first embodiment in the orientation of the photocatalyst unit inside the casing and in the structure of the photocatalyst structure. More specifically, in the second embodiment, the photocatalyst unit 23 is arranged inside the casing 22 with the central axis thereof substantially orthogonal to the general direction of air currents inside the casing 22 and the base plate 16 is fit to the inner wall of the casing 22. Moreover, the disc-shaped member 26 covers the other end of the photocatalyst structure 25 so that no air passes through the other end.

The operation of the ultraviolet radiation air purification system 21 is explained below.

When the ultraviolet radiation source 13 and the exhaust fan 24 are turned on, air currents that flow from the air inlet 22in toward the air outlet 22out are generated inside the casing 22. A first portion of the air enters the photocatalyst structure 25. A second portion of the air goes around the photocatalyst structure 25, flows in the space between the photocatalyst structure 25 and the inner wall of the casing 22, and this portion is discharged from the air outlet 22out. That is, the second portion of the air does not pass through the photocatalyst structure 25. When the first portion of the air passes through the photocatalyst structure 25, air disturbance and air turbulence are created inside the minute cells of the honeycomb structure of the photocatalyst element structure 11. As a result, the chances that the air comes in contact with the photocatalyst increase leading to an increase in the purification performance.

In the photocatalyst element structure 11, because the undulating photocatalyst sheet S6 is arranged at the outer periphery of the photocatalyst structure 25, the second portion of the air that goes around the photocatalyst structure 25 interferes with the ridges and trenches of the undulating photocatalyst sheet S6 leading to generation of air turbulence. This in turn increases the chances that the air comes in contact with the photocatalyst on the undulating photocatalyst sheet S6 leading to an increase in the purification performance.

The ozone generation lamp 18 produces ozone, and the casing 22 is filled with this ozone. The second portion of the air that goes around the photocatalyst structure 25 without passing through the photocatalyst structure 25 is purified by the action of the ozone.

The photocatalyst structure 25 includes the photocatalyst element structure 11 with three overlapping photocatalyst elements 11a, 11b, and 11c rolled in a centrally hollow cylindrical shape. However, the structure of the photocatalyst structure 25 is not limited to this. For example, the photocatalyst structure 25 can have a planar shape and it can be arranged inside the casing 22 with the plane thereof substantially orthogonal to the general direction of air currents inside the casing 22.

The photocatalyst element structures according to the first embodiment and the second embodiment have a honeycomb structure in a cross section. Because of the honeycomb structure, the photocatalyst element structures are fortified so that irrespective of their shape, cylindrical or planar, they do not collapse so easily. As a result, not only the coating of anatase titanium dioxide does not peel off easily, the effective surface area is increased dramatically.

The photocatalyst sheet is made of a flexible porous titanium foil having a non-periodic spongy structure. Because there is no periodicity in any direction, a moire pattern is not produced when a plurality of such photocatalyst sheets is overlapped to form a photocatalyst element structure. When such a photocatalyst element structure is exposed to ultraviolet radiation, the intensity of ultraviolet radiation becomes uniform at any place leading to a prevention of degradation in the purification performance.

Moreover, the bonding strength between the photocatalyst sheet made of a titanium foil and anatase titanium dioxide is high. Therefore, the coating of anatase titanium dioxide does not peel off easily from the photocatalyst sheet.

The photocatalyst sheet has complicated labyrinth channels in the thickness direction so that the surface area increases as compared to a simple mesh structure.

Moreover, the photocatalyst sheet is flexible and it can be bent, curled, or rolled as per the requirement when used in an ultraviolet radiation air purification system.

There is no two-dimensional space between the adjacent photocatalyst sheets. On the contrary, numerous minute cells are formed in the photocatalyst element structures. Air passes through these minute cells when passing through the photocatalyst element structures so that the chances that the air comes in contact with the photocatalyst are increased leading to an increase in the purification performance.

Furthermore, no spacers are required between the adjacent photocatalyst sheets so that the number of components can be reduced leading to a reduction in the manufacturing costs.

Figure 9:
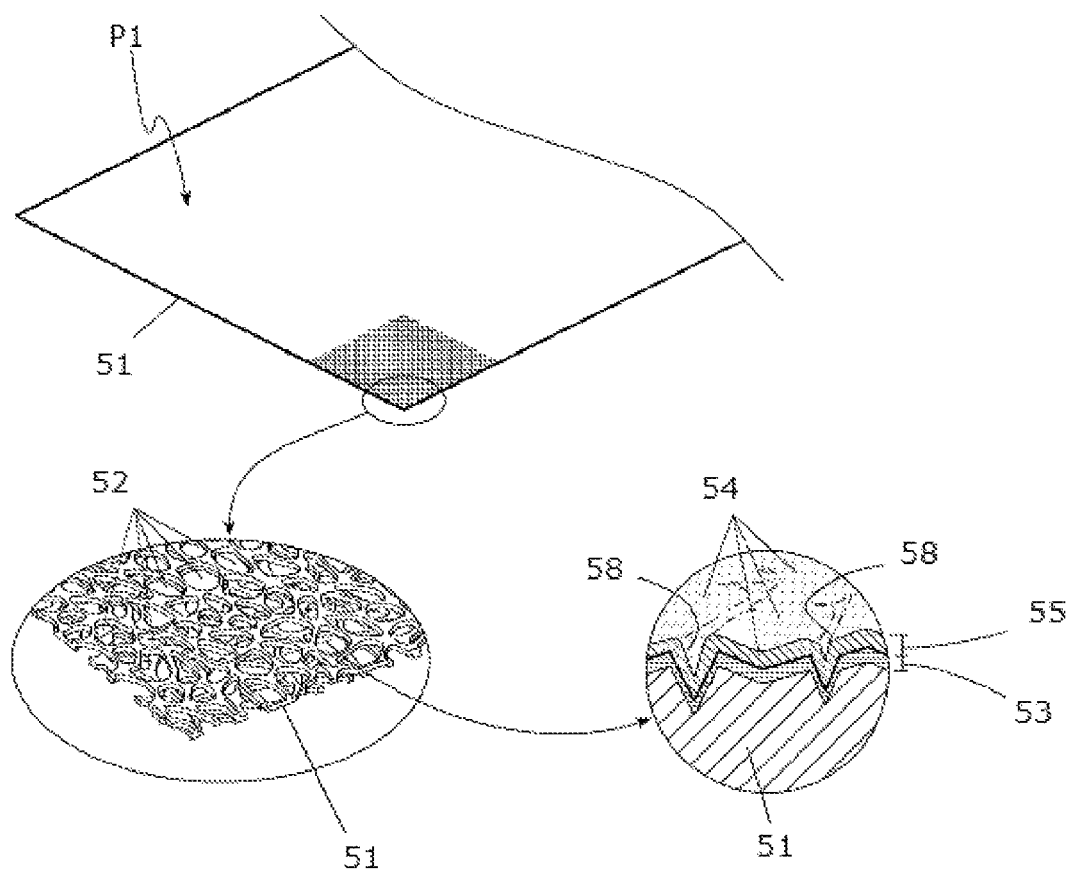
FIG. 9 illustrates a photocatalyst sheet according to a third embodiment of the present invention.

FIG. 9 illustrates a photocatalyst sheet P1 according to a third embodiment of the present invention. The photocatalyst sheet P1 is made of a porous titanium foil 51. The porous titanium foil 51 has a non-periodic spongy structure in which a number of minute cavities 52 communicate from one surface to the other surface. The non-periodic spongy structure is formed by performing etching in non-periodic patterns from one or both the surfaces of a titanium foil. A titanium oxide base 53 is formed on the surface of the porous titanium foil 51 with an anodized film. Finally, a photocatalyst layer 55 is formed by baking anatase titanium dioxide particles 54 on the titanium oxide base 53.

Figure 10:
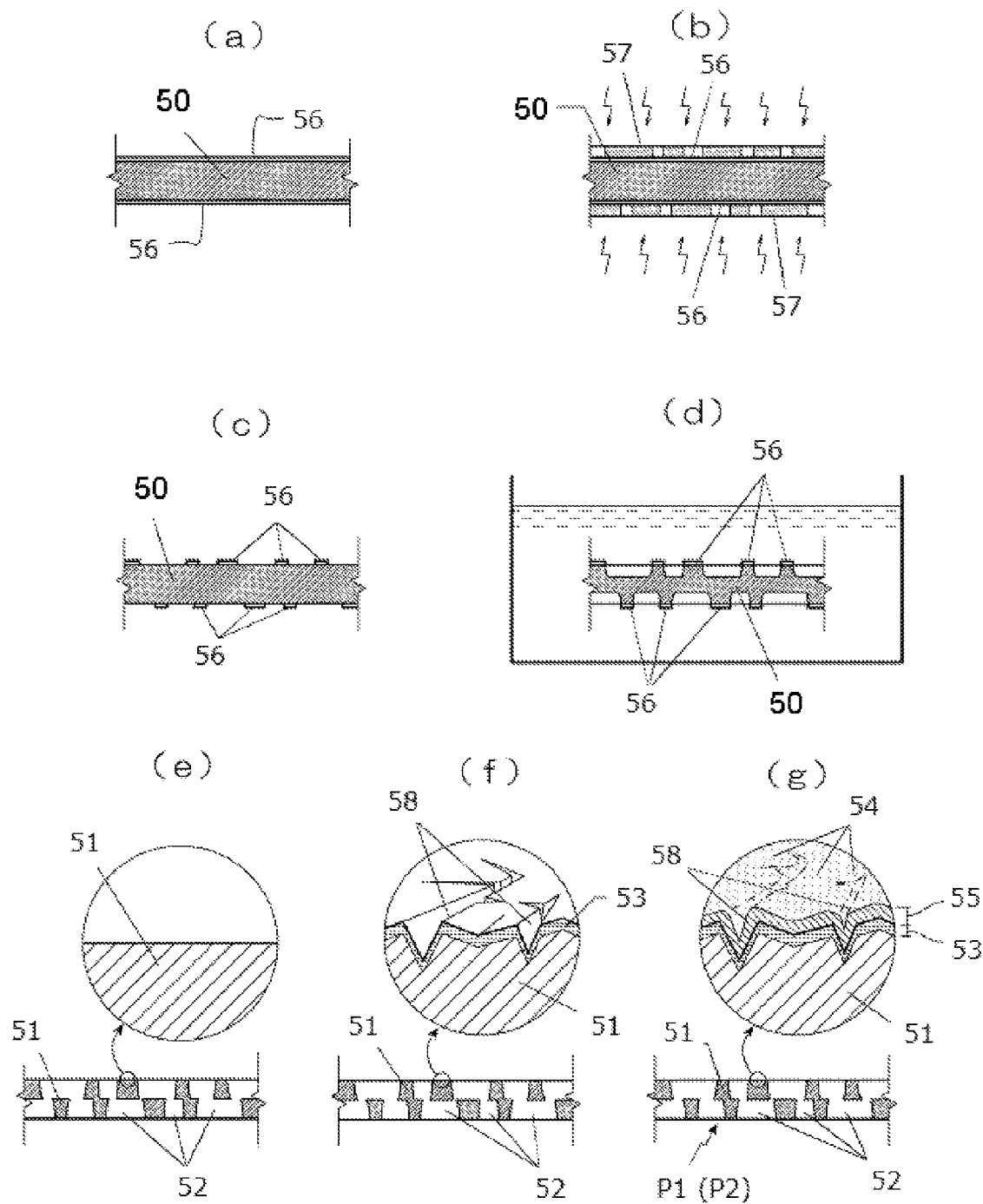
FIG. 10 is an explanatory view for explaining a method of manufacturing the photocatalyst sheet shown in FIG. 9.

FIG. 10 depicts a method of manufacturing the photocatalyst sheet P1.

First, etching processing is performed in order to form the minute cavities 52 in a non-porous titanium foil 50. The titanium foil 50 is obtained by rolling pure titanium. The etching processing includes a process of applying a photoresist material 56 on both the surfaces of the titanium foil 50 (see (a) in FIG. 10), a process of overlaying masking films 57 on which non-periodic patterns have been formed on the photoresist material 56 and exposing the photoresist material 56 (see (b) in FIG. 10), a process of washing away the unexposed portions of the photoresist material 56 and causing the exposed portions of the photoresist material 56 to remain behind (see (c) in FIG. 10), a process of dipping the titanium foil 50 with the non-periodic patterns masked thereon in etching liquid and corroding half of the titanium foil 50 from each surface in the thickness direction to form the minute cavities 52 that communicate from one surface to the other surface of the titanium foil 50 to obtain the porous titanium foil 51 (see (d) in FIG. 10).

Particularly, no periodicity is produced when the non-periodic spongy structure is formed by performing etching processing from both the surfaces of the titanium foil 50. In other words, when the etching processing is performed from both the surfaces of the titanium foil 50, minute cavities of different shapes and sizes are formed on each of the surfaces of the titanium foil 50. As a result, complicated labyrinth shaped minute cavities 52 are formed in the thickness direction of the porous titanium foil 51 and the surface area is increased as compared to a simple mesh structure. The porosity of the photocatalyst sheet P1 is between about 50% to about 80%. In an enlarged view, the surface of the photocatalyst sheet P1 is substantially flat at this stage as shown in (e) in FIG. 10.

Subsequently, anodization processing for forming the titanium oxide base 53 on the surfaces of the porous titanium foil 51 is performed. The anodization processing includes applying, in a phosphoric acid bath (for example, water containing 3% phosphoric acid), voltage between the porous titanium foil 51 as an anode and a not shown cathode. When voltage is applied in this manner, as shown in (f) in FIG. 10, the surface of the porous titanium foil 51 is oxidized and an anodic oxide film is formed. The anodic oxide film is formed not only on the surface of the porous titanium foil 51, but it is also formed on the internal walls of the minute cavities 52. That is, the anodic oxide film is formed on every portion of the porous titanium foil 51 that is in contact with the liquid in the phosphoric acid bath. Subsequently, a heat treatment of heating the porous titanium foil 51 in atmospheric conditions at 550° C.

for three hours is performed. As a result, the anodic oxide film is converted into the titanium oxide base 53.

If the surface of the porous titanium foil 51 is seen in an enlarged view at this stage, a number of minute cracks 58 can be seen. These cracks were not present at a time point of completion of the etching process, that is, the surface was substantially flat at that time point. In other words, the minute cracks 58 are developed due to the anodization processing and the heating treatment.

When titanium is subjected to anodic oxidation to form an anodic oxide film, the anodic oxide film produces a light having different color due to interference depending on its thickness. For example, it is known that the anodic oxide film produces violet light when its thickness is about 70 nm, produces green light when its thickness is about 150 nm, and produces pink light when its thickness is about 200 nm. In the third embodiment, an anodic oxide film having a thickness somewhere between 70 nm and 150 nm was formed.

Finally, baking processing for attaching the anatase titanium dioxide particles 54 on the titanium oxide base 53 is performed. More specifically, when the porous titanium foil 51 with the titanium oxide base 53 formed thereon is dipped in the slurry containing the anatase titanium dioxide particles 54 and the slurry is heated to about 550° C., as shown in (g) in FIG. 10, the photocatalyst layer 55 is formed on both the surfaces of the porous titanium foil 51 and also on the internal walls of the minute cavities 52. When the titanium oxide base 53 and the photocatalyst layer 55 are formed in this manner, there takes place an extremely strong binding between titanium oxides in each of these layers and the photocatalyst layer 55 does not peel off easily.

Moreover, presence of the minute cavities 52 makes the surface of the porous titanium foil 51 uneven with complicated bumps and holes. As a result, the minute cracks 58 of micron scale are formed in the titanium oxide base 53 that is an anodized film. Therefore, not only the photocatalyst layer 55 is bonded to it very strongly, but also the surface area is increased leading to an increase in the purification performance.

Furthermore, when the porous titanium foil 51 is exposed to ultraviolet radiation, irregular reflection and/or scattering takes place at the boundary between the photocatalyst layer 55 and the titanium oxide base 53 whereby the ultraviolet radiation can be used more efficiently.

In addition, the photocatalyst sheet made of a titanium foil is lightweight and excellent in heat and chemical resistances. Therefore, it can be used even in harsh conditions.

Figure 11:
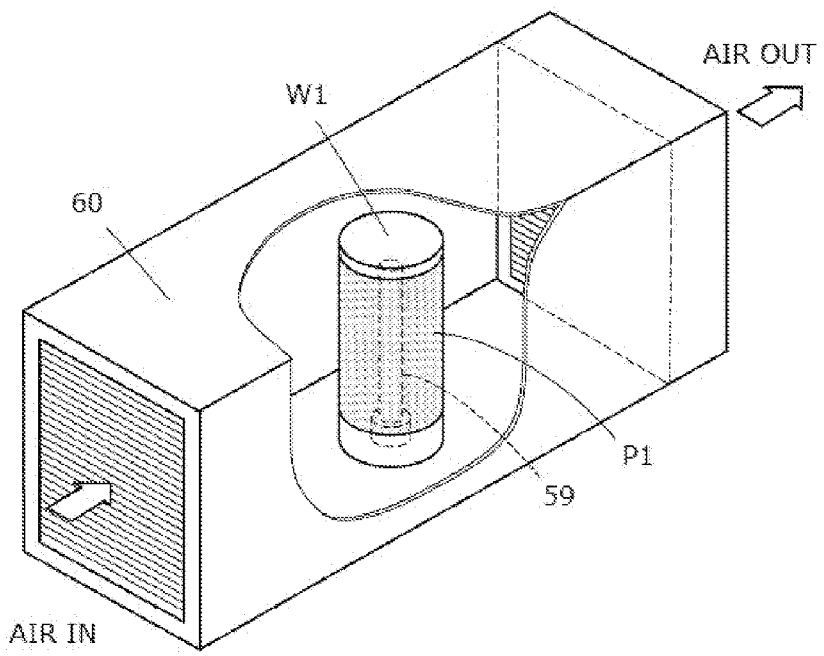
FIG. 11 is a perspective view of an air purification system that employs the photocatalyst sheet shown in FIG. 9.

Subsequently, as shown in FIG. 11, a photocatalyst unit W1 is prepared by rolling the photocatalyst sheet P1 in a centrally hollow cylindrical shape and arranging an ultraviolet radiation source 59 in the hollow portion. The photocatalyst unit W1 is then arranged inside a casing 60 of an air purification system in the path of the air currents flowing inside the casing 60.

If the photocatalyst sheet P1 is in a planar shape, ultraviolet radiation sources are provided so that both the surfaces of the photocatalyst sheet P1 are exposed to ultraviolet radiation. In other words, a multilayer structure of photocatalyst sheets can be made to enhance a photocatalytic effect.

Figure 12:
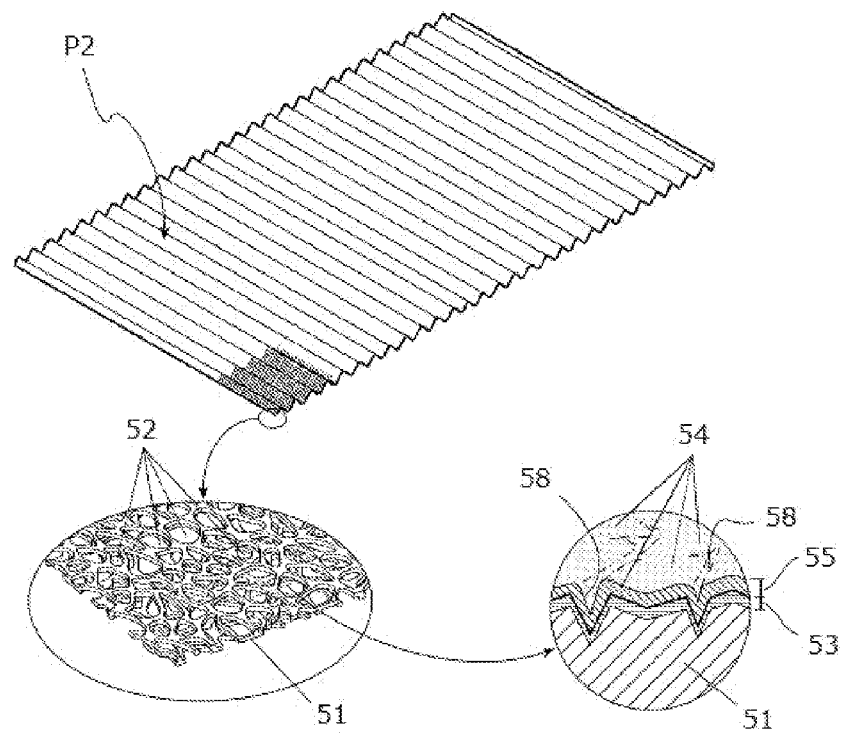
FIG. 12 is a perspective view of a photocatalyst sheet according to a fourth embodiment of the present invention.

FIG. 12 illustrates a photocatalyst sheet P2 according to a fourth embodiment of the present invention. As shown in FIG. 12, the photocatalyst sheet P2 has an undulating shape with substantially parallel and alternating ridges and trenches that extend substantially in one direction. The rest of the structure of the photocatalyst sheet P2 is similar to the photocatalyst sheet P1 according to the third embodiment.

In the fourth embodiment, in order to form the photocatalyst sheet P2 into an undulating shape, after performing the anodization processing and before performing the heat treatment, the photocatalyst sheet P2 is subjected to a forming processing of press machining to form the substantially parallel and alternating ridges and trenches that extend in substantially one direction of the photocatalyst sheet P2. The desired effect is obtained when the forming processing is performed after performing the etching processing and before performing the baking processing of baking the anatase titanium dioxide particles 54 on the titanium oxide base 53. For example, the forming processing can be performed after performing the etching processing and before performing the anodization processing.

Figure 13:
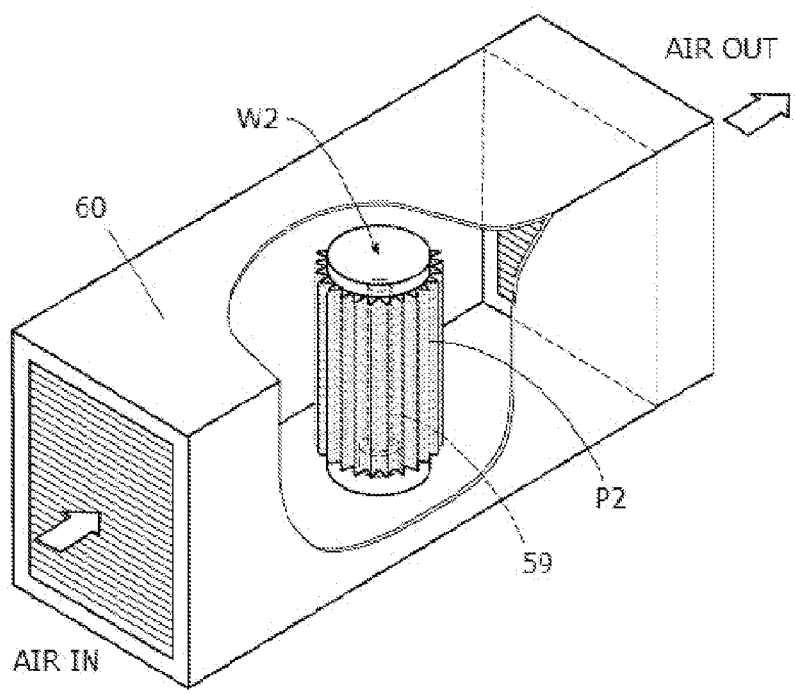
FIG. 13 is a perspective view of an air purification system that employs the photocatalyst sheet shown in FIG. 12.

Subsequently, as shown in FIG. 13, a photocatalyst unit W2 is prepared by rolling the photocatalyst sheet P2, and the photocatalyst unit W2 is then arranged inside the casing 60 of an air purification system in the path of the air currents flowing inside the casing 60.

Figure 14:
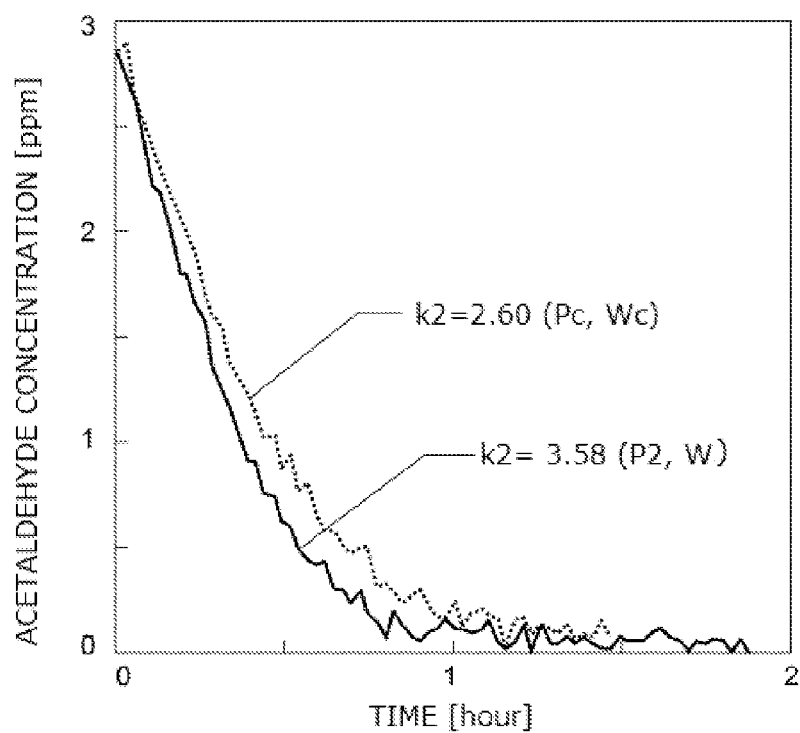
FIG. 14 is a graph for explaining experimental results.
Figure 15:
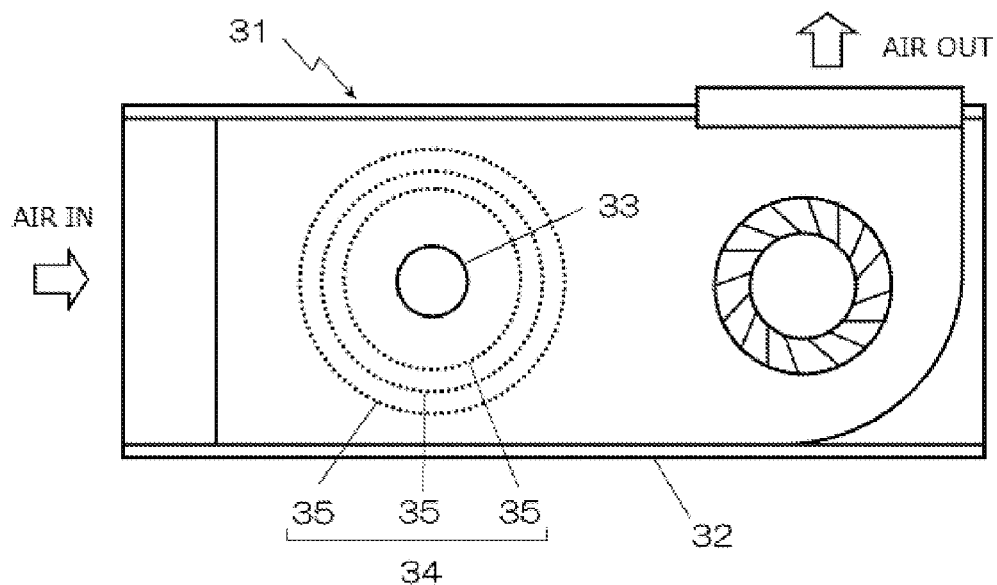
FIG. 15 is a perspective view of a conventional fluid purification system.
Figure 16:
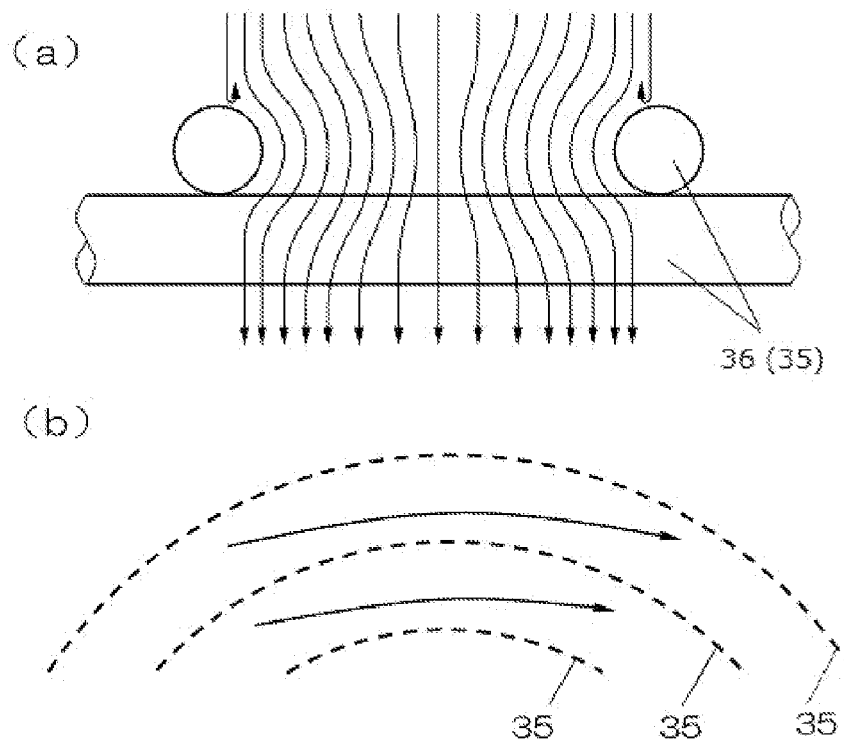
FIG. 16 schematically illustrates how air passes through a photocatalyst element structure of the conventional fluid purification system.

FIG. 14 is a graph for explaining the results obtained in an experiment for verifying the performance of the photocatalyst unit W2. In this experiment, a not shown photocatalyst unit W was prepared by overlapping two photocatalyst sheets P2 and rolling the photocatalyst sheets P2 in a centrally hollow cylindrical shape and arranging an ultraviolet radiation source of wavelength 254 nm inside the hollow of the photocatalyst unit W. The photocatalyst unit W was then arranged inside a 1-cubic-meter enclosed space and air was blown on the photocatalyst unit W at a speed of 5.5 m/s. A change in the concentration of acetaldehyde over time in the enclosed space was monitored. From the result obtained in the monitoring, a decomposition factor k2 was calculated for the photocatalyst unit W.

Moreover, a not shown photocatalyst unit Wc was prepared by overlapping two photocatalyst sheets Pc and rolling the photocatalyst sheets Pc in a centrally hollow cylindrical shape. The photocatalyst sheet Pc differed in structure from the photocatalyst sheets P2 in that it was not subjected to the anodization processing. The same experiment as on the photocatalyst unit W was then performed on the photocatalyst unit Wc, and the decomposition factor k2 was calculated for the photocatalyst unit Wc. The ultraviolet radiation transmittance of each of the photocatalyst units W and Wc was 12%.

The decomposition factor k2 for the photocatalyst unit Wc and the photocatalyst unit W was 2.60 and 3.58, respectively. Thus, the photocatalyst unit W that included the photocatalyst sheets P2 according to the second embodiment exhibited much better purification performance than the photocatalyst unit Wc.

As explained above, the photocatalyst sheets according to the third embodiment and the fourth embodiment are flexible and therefore, they can be bent, curled, or rolled in a desired shape depending on where they are to be used.

Moreover, the photocatalyst sheet has a non-periodic spongy structure with minute cavities that communicate from one surface to the other surface so that the surface area is increased as compared to the simple wire mesh or perforated metal.

The photocatalyst sheet has a photocatalyst layer on a titanium oxide base. The titanium dioxide in the titanium oxide base and the photocatalyst layer are bonded extremely strongly so that the photocatalyst layer does not peel off easily.

Moreover, the surface of the photocatalyst sheet is uneven with complicated bumps and holes. As a result, minute cracks of micron scale are formed in the titanium oxide base. Therefore, not only the photocatalyst layer is bonded to it very strongly, but also the surface area is increased leading to an increase in the purification performance.

Furthermore, when the photocatalyst sheet is exposed to ultraviolet radiation, irregular reflection and/or scattering takes place at the boundary between the photocatalyst layer and the titanium oxide base whereby the ultraviolet radiation can be used more efficiently.

In addition, the photocatalyst sheet is lightweight, and excellent in heat and chemical resistances. Therefore, it can be used even in harsh conditions.

The photocatalyst sheets according to the third embodiment and the fourth embodiment can be used in the first embodiment and the second embodiment.

INDUSTRIAL APPLICABILITY

The photocatalyst sheets according to the embodiments can be used in purification systems that can be installed in hospitals, factories, houses, offices, etc. for purifying air or water.

EXPLANATIONS OF LETTERS OR NUMERALS

1, 21 ultraviolet radiation air purification system
2 casing
3 exhaust fan
10 photocatalyst unit
11 photocatalyst element structure
12 photocatalyst structure
13 ultraviolet radiation source
S1 flat photocatalyst sheet
S2 undulating photocatalyst sheet

The invention claimed is:

1. A photocatalyst element structure comprising:
   a photocatalyst element including a flat photocatalyst sheet and an undulating photocatalyst sheet overlapped on the flat photocatalyst sheet, wherein
   the flat photocatalyst sheet and the undulating photocatalyst sheet include a porous titanium foil having a non-periodic spongy structure impregnated with anatase titanium dioxide particles.

2. The photocatalyst element structure according to claim 1, comprising a plurality of the photocatalyst elements arranged so that the flat photocatalyst sheet and the undulating photocatalyst sheet alternate.

3. The photocatalyst element structure according to claim 1, wherein the porous titanium foil is flexible.

4. The photocatalyst element structure according to claim 1, wherein the porous titanium foil is formed by subjecting a titanium foil to etching processing in non-periodic patterns from one or both surfaces of the titanium foil.

5. The photocatalyst element structure according to claim 1, wherein the undulating photocatalyst sheet has substantially parallel and alternating ridges and trenches that extend in one direction, and the photocatalyst element being rolled in a centrally hollow cylindrical shape so that the ridges and the trenches of the undulating photocatalyst sheet extend in a direction of a central axis of the cylindrical photocatalyst element.

6. The photocatalyst element structure according to claim 5, wherein the undulating photocatalyst sheet is located on an outer periphery of the cylindrical photocatalyst element.

7. An ultraviolet radiation air purification system comprising:
   a casing having an air inlet and an air outlet;
   a photocatalyst element structure that is arranged inside the casing for purifying air inside the casing; and an ultraviolet radiation source that irradiates ultraviolet radiation to activate a photocatalyst of the photocatalyst element structure, wherein the photocatalyst element structure includes a photocatalyst element including a flat photocatalyst sheet and an undulating photocatalyst sheet overlapped on the flat photocatalyst sheet, and the flat photocatalyst sheet and the undulating photocatalyst sheet include a porous titanium foil having a non-periodic spongy structure impregnated with anatase titanium dioxide particles as the photocatalyst.

8. The ultraviolet radiation air purification system according to claim 7, comprising a plurality of photocatalyst elements arranged so that the flat photocatalyst sheet and the undulating photocatalyst sheet alternate.

9. The photocatalyst element structure according to claim 7, wherein the porous titanium foil is flexible.

10. The ultraviolet radiation air purification system according to claim 7, wherein the porous titanium foil is formed by subjecting a titanium foil to etching processing in non-periodic patterns from one or both surfaces of the titanium foil.

11. The ultraviolet radiation air purification system according to claim 7, wherein the undulating photocatalyst sheet has substantially parallel and alternating ridges and trenches that extend in one direction, and the photocatalyst element being rolled in a centrally hollow cylindrical shape so that the ridges and the trenches of the undulating photocatalyst sheet extend in a direction of a central axis of the cylindrical photocatalyst element.

12. The ultraviolet radiation air purification system according to claim 11, wherein the undulating photocatalyst sheet is located on an outer periphery of the cylindrical photocatalyst element.

13. The ultraviolet radiation air purification system according to claim 7, wherein the photocatalyst element being rolled in a centrally hollow cylindrical shape, the ultraviolet radiation source being arranged inside a hollow portion of the cylindrical photocatalyst element, one end of the cylindrical photocatalyst element being closed with a closing member so that air does not pass through that end in the hollow portion and other end of the cylindrical photocatalyst element being open so that air entering into the hollow portion through walls of the photocatalyst element is discharged through that end, and the ultraviolet radiation air purification system further comprising a guide member arranged inside the casing to guide air entering the casing onto the photocatalyst element structure.

14. The ultraviolet radiation air purification system according to claim 7, wherein the ultraviolet radiation source includes one or both of a sterilization lamp with a central wavelength of 254±10 nanometers and an ozone generation lamp with a central wavelength of 185±10 nanometers.

* * * * *